United States Patent
Quis et al.

(10) Patent No.: US 6,960,638 B2
(45) Date of Patent: Nov. 1, 2005

(54) DEPOT POLYMERIZATION STARTER BEADS

(75) Inventors: Peter Quis, Darmstadt (DE); Heike Heeb, Bickenbach (DE); Helmut Schwind, Hanau (DE); Harald Draeger, Rodenbach (DE)

(73) Assignee: Roehm GmbH & Co. KG, Darmstadt (DE)

( * ) Notice: Subject to any disclaimer, the term of this patent is extended or adjusted under 35 U.S.C. 154(b) by 0 days.

(21) Appl. No.: 10/485,253

(22) PCT Filed: Jul. 9, 2002

(86) PCT No.: PCT/EP02/07604

§ 371 (c)(1),
(2), (4) Date: Feb. 6, 2004

(87) PCT Pub. No.: WO03/014173

PCT Pub. Date: Feb. 20, 2003

(65) Prior Publication Data

US 2004/0198939 A1 Oct. 7, 2004

(30) Foreign Application Priority Data

Aug. 8, 2001 (DE) .......................................... 101 37 968

(51) Int. Cl.$^7$ ............................................. C08F 120/18
(52) U.S. Cl. ................................ 526/329.7; 526/329.2; 526/319; 526/228; 526/229; 526/232.1; 526/232.3; 523/116; 525/309

(58) Field of Search ................................ 526/319, 229, 526/323.2, 326

(56) References Cited

U.S. PATENT DOCUMENTS

| | | | | |
|---|---|---|---|---|
| 3,444,270 A | * | 5/1969 | Aliberti et al. | 525/253 |
| 3,784,501 A | * | 1/1974 | Pettit, Jr. | 524/291 |
| 3,842,058 A | * | 10/1974 | Milkovich et al. | 525/292 |
| 4,129,545 A | * | 12/1978 | Sunamori et al. | 524/555 |
| 4,284,707 A | * | 8/1981 | Nagasawa et al. | 430/196 |
| 4,677,173 A | * | 6/1987 | Holle et al. | 526/193 |
| 5,142,008 A | * | 8/1992 | Holle et al. | 526/193 |
| 5,210,164 A | * | 5/1993 | Komai et al. | 526/230.5 |
| 5,276,070 A | * | 1/1994 | Arroyo | 523/117 |
| 5,285,229 A | * | 2/1994 | Kamata | 396/6 |
| 6,475,688 B1 | * | 11/2002 | Tamura et al. | 430/108.3 |

FOREIGN PATENT DOCUMENTS

| | | |
|---|---|---|
| DE | 23 55 813 | 6/1975 |
| EP | 0477708 A2 * | 9/1991 |
| EP | 1 022 295 | 7/2000 |
| JP | 60066265 * | 4/1985 |
| WO | 01 30872 | 5/2001 |

* cited by examiner

*Primary Examiner*—Tatyana Zalukaeva
(74) *Attorney, Agent, or Firm*—Oblon, Spivak, McClelland, Maier & Neustadt, P.C.

(57) ABSTRACT

The invention relates to polymer beads having a high content of diacyl peroxides. A prolongation of the pot life in reaction resins based on high-boiling methacrylate esters is achieved due to this high content of peroxides.

16 Claims, No Drawings

DEPOT POLYMERIZATION STARTER BEADS

FIELD OF THE INVENTION

The invention relates to suspension copolymers composed of methyl methacrylate and of other monomers copolymerizable therewith, which have a high and not previously achieved content of residual peroxides. The beads of the invention with increased residual peroxide content may be used for example in construction chemistry as a polymerization initiator in or redox-curing binders.

PRIOR ART

EP 581 387 (Bristol-Myers Squibb Company) describes a bone cement composed of polymer particles, where the polymer particles are composed of two or more layers, which may comprise a very wide variety of additives. Besides X-ray contrast agents, dyes, antibiotics, bone growth factors, these layers may also comprise polymerization initiators. The polymer particles always have a layer structure. Various polymerization kinetics are achieved by distributing the polymerization initiator over various compartments (see FIG. 7 of EP 581 387) having a shell-type structure.

OBJECT

An object was therefore to provide polymer beads with varying composition of the starting monomers and with maximum contents of homogeneously distributed polymerization initiator, which can be produced without the complicated shell-type structure and can therefore be produced more simply and at lower cost. The beads are also intended to have a wide processing spectrum in monomer-containing reactive resin systems which can be cured by a free-radical route, the intended result being maximum pot life.

The object has been achieved by way of a depot polymerization initiator bead according to the claims.

The bead of the invention has the following advantages:

The open time available for processing of the reactive resin can be controlled effectively by way of the ratio of peroxide concentration to polymer and by way of the solubility of the beads in the reactive resin.

Because the supply of free radicals is uniform, both spatially and chronologically, curing of the reactive resin is better, when comparison is made with the conventional polymerization initiators.

Better surface dryness of the formulated coating systems in situ is also achieved.

Composition of the beads of the invention:
1. from 1–99% by weight of a derivative of an unsaturated carboxylic acid of the formula (I),

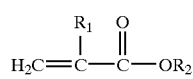
(I)

where:
$R_1$=H or $CH_3$
$R_2$=methyl, ethyl
2. from 99–1% by weight of a derivative of an unsaturated carboxylic acid of the formula (II),

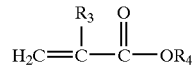
(II)

where:
$R_3$=H or $CH_3$
$R_4$=an aliphatic radical having from 4–6 carbon atoms, for example:
n-butyl, isobutyl, tert-butyl, pentyl, hexyl and methylcyclopentyl, cyclohexyl, and also terahydrofurfuryl or isobornyl
3. from 1–10% by weight of a peroxide or of a peroxide mixture.
From 3–10% by weight of a peroxide or of a peroxide mixture are preferred. From 5–10% by weight of a peroxide or of a peroxide mixture are particularly preferred.
By way of example, benzoyl peroxides and other diacyl peroxides are used as peroxide or peroxide mixture.
4. from 1–15% of one or more monomers copolymerizable with the monomers of 1. or of 2., where the percentages of 1.–4. give a total of 100%.
By way of example, copolymerizable monomers used are styrene or styrene derivatives, such as methyl styrene or maleic acid or maleic anhydride.

The average diameter of the beads is from 50 to 200 µm. The diameter was determined by means of laser diffraction spectroscopy, using a Malvern Mastersizer Microplus (measurement range: from 0.05 to 555 µm).

Residual monomer content was measured by means of gas-chromatographic head-space analysis, a method for determining vaporizable constituents in liquids and solids (inter alia of monomers in thermoplastics).

The viscosity number VN (or Staudinger function) is the relative change in viscosity, divided by concentration, of a 0.5% strength solution of the copolymer in chloroform, based on the solvent, the flow times being determined in a suspended-globe Ubbelohde viscometer, Schott No. 53203 and capillary 0 c to D/N 51562 at 25° C. Chloroform was used as solvent.

$$VN = \left(\frac{t}{t_o} - 1\right) \cdot \frac{1}{c}$$

where:
t=polymer solution flow time in seconds
$t_o$=solvent flow time in seconds
c=concentration in g/100 ccm
Production Specification The production of the copolymers to be used according to the invention is known per se. They may be produced by bulk polymerization or suspension polymerization. Useful information on bulk polymerization is found in Houben-Weyl, Volume E20, Part 2 (1987), page 1145 et seq. The suspension polymerization technique is also described there on page 1149 et seq.

EXAMPLES

Example 1

Production Specification for Depot Peroxide Bead:
37.75 g of aluminum sulfate×14$H_2O$ are dissolved in 3 750 g of demineralized water and heated to 40° C. in a 5 1 polymerization vessel equipped with stirrer, reflux condenser and thermometer. To generate the suspension stabilizer, 166.25 g of a 10% strength aqueous sodium carbonate solution, 0.28 g of sodium $C_{15}$-paraffin sulfonate and 0.272 g of polyethylene glycol (molecular weight from 5 000 to 6 000) are added, with stirring. 1 250 g of a mixture composed of 43.1 parts by weight of methyl methacrylate, 43.1 parts by weight of n-butyl methacrylate, 0.013 part by weight of 2-ethylhexyl thioglycolate and 13.7 parts by weight of 75% strength aqueous dibenzoyl peroxide were then added, with continued stirring. The mixture was then heated to 70° C., polymerized for 40 minutes at 70° C. and for 60 minutes at 77° C. and then cooled to 50° C. At this temperature 36 g of 50% strength sulfuric acid were added to disperse the suspension stabilizer. After further cooling to room temperature, the polymerization beads were filtered off, thoroughly rinsed with demineralized water, and dried in a fluidized-bed dryer at 40° C.

1 391 g of clear polymer beads were obtained with a residual dibenzoyl peroxide content of 10% by weight, determined iodometrically.

Example 2

Curing Experiment with a Reactive Resin Based on High-Boiling (Meth)Acrylate (HB):

The peroxide bead described in example 1 with a content of 10% of dibenzoyl peroxide was introduced within a period of 2 minutes, with stirring, as reaction initator in a reactive resin based on high-boiling (meth)acrylates at a concentration of 10% (=1% of active dibenzoyl peroxide). The activated reactive resin was then poured, at a layer thickness of about 2 mm, onto a concrete substrate. It cured tack-free within about 30 minutes and had a pot life of from 15 to 18 minutes.

Example 3

Comparative Experiment with Phlegmatized Dibenzoyl Peroxide:

The experiment of example 2 was repeated, but the initiator used comprised 2% of dibenzoyl peroxide phlegmatized at 50% strength in dicyclohexyl phthalate (BP-50-FT, Interox). The reactive resin likewise cured within about 30 minutes. However, the pot life was only about 8–10 minutes.

Pot life times/conversion times of binders -
Based on: MMA, nBuMA or high-boilers with various depot peroxide beads

| Resin/ PL + CT* *pot life/ curing time | BPO-50% -powder- | Depot bead (10% strength peroxide) | | | | |
|---|---|---|---|---|---|---|
| | | MMA | MMA + 10 ppm BDMA | MMA/BuMA = 50/50 | MMA/BuMA = 75/25 | MMA/BuMA = 25/75 |
| % by weight | 2 | 10 | 10 | 10 | 10 | 10 |
| DGD 523 "MMA" | 8–10'/ 18–23' 116° C.-17' sl. yellowish | poor sol. ~50/75–100' clear, sl. moist | poor sol. ~55/85–110' edge region moist surf. rough | gel-like 6'/15–20' 134° C.-15' lumps of gel | 6–8'/18–22' 119° C.-18' v. rough surf. | insoluble |
| NGB 52 "BuMA" | 8–10'/ 30–40' 90° C.-19' sl. yellowish | >5 h termination | >5 h termination | 15'/35' yellowish | 70'/120–170' 90° C.-90' clear | poor sol./gel-like 7–9'/20–30' surf. rough |
| GFG 330 HS | 4–6'/15–20' sl. yellowish | >5 h termination | >5 h termination | 10–12'/22–30' 104° C.-17' clear | 45' non-unif. no curing | gel-like 5–6'/13–18' 96° C.-11' |

Degadur 523 (DGD 523) is marketed by Rohm GmbH & Co. KG and is a reactive resin produced from low-boiling monomers. The monomer phase of Degadur 523 is composed of methyl methacrylate, 2-ethylhexyl acrylate and polyfunctional methacrylates. NGB52 is a reactive resin based on moderate-boiling-point monomers (e.g. butyl methacrylate). GFG 330 HS is a reactive resin based on high-boiling monomers, e.g. tetrahydrofurfuryl methacrylate.

The table gives the pot life first and secondly the curing time. Pot life should be from 50 to 20 minutes, and curing time should be from 25 to 60 minutes. The coating composition is a homogeneous mixture which is easy to apply.

What is claimed is:

1. A suspension copolymer, comprising:
    in copolymerized form the following components (a), (b) and (c):
    (a) more than 1% by weight of a derivative of an unsaturated carboxylic acid of the formula (I),

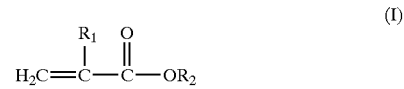

wherein
    $R_1$=H or $CH_3$, and
    $R_2$=methyl, ethyl;
    (b) more than 1% by weight of a derivative of an unsaturated carboxylic acid of the formula (II),

wherein
    $R_3$=H or $CH_3$, and $R_4$=n-butyl, isobutyl; and (c) from 0–15% of one or more monomers copolymerizable with the monomers (a) or (b);

said copolymer containing a residual amount of from 1–10% by weight of at least one polymerization initiator selected from the group consisting of peroxides and peroxide mixtures;

wherein a sum of the amounts of (a), (b), (c) and said polymerization initiator is 100%;

wherein said copolymer is in the form of beads; and wherein said polymerization initiator is homogeneously distributed in said beads.

2. The suspension copolymer according to claim 1, which does not have a shell structure.

3. The suspension copolymer according to claim 1, wherein said polymerization initiator is present in an amount of from 3–10% by weight.

4. The suspension copolymer according to claim 1, wherein polymerization initiator is present in an amount of from 5–10% by weight.

5. The suspension copolymer according to claim 1, wherein said polymerization initiator is a peroxide.

6. The suspension copolymer according to claim 1, wherein said polymerization initiator is a mixture of peroxides.

7. The suspension copolymer according to claim 1, wherein said polymerization initiator is a benzoyl peroxide.

8. The suspension copolymer according to claim 1, wherein said polymerization initiator is a diacyl peroxide.

9. The suspension copolymer according to claim 1, wherein component (c) is present.

10. The suspension copolymer according to claim 1, wherein component (c) is a member selected from the group consisting of styrene, styrene derivatives, maleic acid, maleic anhydride and mixtures thereof.

11. The suspension copolymer according to claim 1, having an average diameter of from 50 to 200 $\mu$m.

12. A composition, comprising:

a polymerizable monomer and the suspension copolymer according to claim 1.

13. A floorcovering composition, comprising:

the suspension copolymer according to claim 1.

14. A dental filling composition, comprising:

the suspension copolymer according to claim 1.

15. A cold-plastic road-marking composition, comprising:

the suspension copolymer according to claim 1.

16. A method of curing a reactive resin, comprising:

contacting the suspension copolymer according to claim 1 with a reactive resin.

* * * * *